United States Patent [19]

Terpening

[11] 4,176,665
[45] Dec. 4, 1979

[54] STOCKING KNEE BRACE
[75] Inventor: George I. Terpening, Telford, Pa.
[73] Assignee: Acro Matic Inc., Warrington, Pa.
[21] Appl. No.: 843,810
[22] Filed: Oct. 20, 1977
[51] Int. Cl.$^2$ .............................................. A61F 1/60
[52] U.S. Cl. ........................................ 128/165; 2/239; 128/80 R
[58] Field of Search .............. 128/165, 239, 240, 241, 128/80 R, 77

[56]  References Cited
U.S. PATENT DOCUMENTS

| 1,693,141 | 11/1928 | Ducat | 2/240 |
| 3,945,046 | 3/1976 | Stromgren | 128/165 |

FOREIGN PATENT DOCUMENTS

| 16644 | of 1906 | United Kingdom | 128/165 |
| 206271 | 8/1923 | United Kingdom | 128/165 |
| 318668 | 9/1929 | United Kingdom | 128/165 |

Primary Examiner—Robert W. Michell
Assistant Examiner—Milford A. Juten
Attorney, Agent, or Firm—William B. Noll

[57] ABSTRACT

A stocking knee brace of the type to be used by athletes with knee problems. Such brace comprises a one-piece stocking sheath adapted to cover at least a portion of the foot up to the mid-thigh region. The sheath, in its preferred form, is knitted and characterized by full dimensional stretch. Such sheath is maintained in compression and tension about the wearer's leg by the elastic nature of the knitted stocking and by a foot encircling strap within said sheath. The knee-joint position of such sheath is provided with two vertically elongated openings, one on each side of the knee-joint, and fastening means to provide additional lateral, compressive pressure to such knee-joint.

5 Claims, 3 Drawing Figures

STOCKING KNEE BRACE

BACKGROUND OF THE INVENTION

The present invention is directed to a stocking knee brace to be worn by athletes with knee problems. More particularly, such knee brace is designed to support the damaged lateral cartilage about the knee-joint.

The knee-joint is a complex structure which is characterized in medical journals as a joint formed by the femur, tibia, and patella (knee cap). It belongs to the class of hinge-joints, although the movements that take place are much more complex than the simple motion of a hinge, the condyles of the femur partly rolling, partly sliding over the flat surfaces on the upper end of the tibia, and the acts of straightening and of bending the limb being finished and begun respectively by a certain amount of rotation. The cavity of the joint is very intricate, and it consists really of three joints fused into one, but separated in part by ligaments and folds of the synovial membrane. The ligaments which bind the bones together are extremely strong, and include the internal and the external lateral ligaments, a weak posterior ligament, a very strong patellar ligament uniting the patella to the front of the tibia, two crucial ligaments in the interior of the joint, and two fibro-cartilages which are interposed between the surfaces of tibia and femur at their edge. The cartilage on the femur and tibia ends provides a surface for smooth gliding motion.

While the knee-joint has a great degree of strength, its strength and stability is often challenged by the physical activities participated in by scholastic and professional athletes. As a consequence, a troublesome condition may develop in such joint. Such condition consists of the loosening of one of the fibro-cartilages lying at the end of the tibia, especially of that on the inner side of the joint. The cartilage may either be loosened from its attachment and tend to slip beyond the edges of the bones, or it may become folded on itself. In either case, it tends to cause locking of the joint when sudden movements are made. This causes temporary inability to use the joint until the cartilage is replaced by forcible straightening, and the ligaments binding the bones together are strengthened.

Knee supports or braces of various types are and have been in use by athletes with knee injuries or weak knees requiring support. This is particularly true in sporting activities such as football and basketball. Typically, such supports or braces use longitudinally extending metal stays along the sides of the knee or metal hinges at the knee-joint. An example of such a brace is illustrated and described in U.S. Pat. No. 3,817,244 to Taylor. As stated by such patent, the knee brace thereof comprises inner and outer bracing structures, each comprising two substantially rigid generally planar and elongated arms. Upper securing means secures one arm of each bracing structure parallel to the wearer's upper leg above the knee for movement with the upper leg and limited motion parallel to the upper leg, and lower securing means secures the outer arm of each bracing structure parallel to the wearer's lower leg below the knee for movement with the lower leg and limited motion parallel to the lower leg. Each bracing structure has a first arm bifurcated to provide two generally parallel plate portions; the second arm has an end portion received between the plate portions for articular motion of the second arm relative to the first arm within a plane parallel to the planes of the plate portions; the plate portions prevent motion of the second arm out of the plane.

Unfortunately, such braces as taught by Taylor may be heavy and cumbersome causing the wearer thereof to be restricted in the flexing of his knee, thus limiting his athletic activities or participation.

Others have attempted to overcome the restrictions resulting from the use of metal stays or hinges by their elimination completely. By way of example, U.S. Pat. No. 3,945,046 to Stromgren teaches a knee support comprising a tubular, elastic sheath to be slipped over the knee. Pressure is applied by a pair of elastic straps anchored to the sheath and held in place by fasteners. The straps in their operative positions extend in criss-cross fashion over the inwardly facing sidewall portion of the sheath, and in directions to duplicate the physiologic stability of the medial knee ligament complex.

Each of the above brace or support is characterized by a device acting solely at or about the knee-joint. In contrast to such brace or support the stocking knee brace of the present invention utilizes supportive action from the entire lower leg. Such a feature will be apparent in the description to follow.

SUMMARY OF THE INVENTION

This invention relates to a new stocking knee brace which is light-weight and convenient to wear by athletes while actively engaged in their chosen sport. Such knee brace is particularly suited for athletes involved in football and basketball where knee problems are a major concern. The knee brace of this invention is adapted to support the lateral cartilage of the knee-joint. Said knee brace comprises a form fitting, preferably knitted, sheath adapted to encircle the wearer's leg from a position below the ankle to a position above the knee. Within such sheath there is provided an elastic strap, which strap in its operative position is engaged by the wearer's foot, preferably at the instep thereof. At a mid-position along said sheath, i.e. the sheath portion encircling the knee-joint, a pair of vertical openings are provided, one on each side. In the operative or protective position of said stocking knee brace, compressive pressure about the knee-joint is provided by fastening means adjacent said openings.

DETAILED DESCRIPTION OF PREFERRED EMBODIMENT

Figure 1:
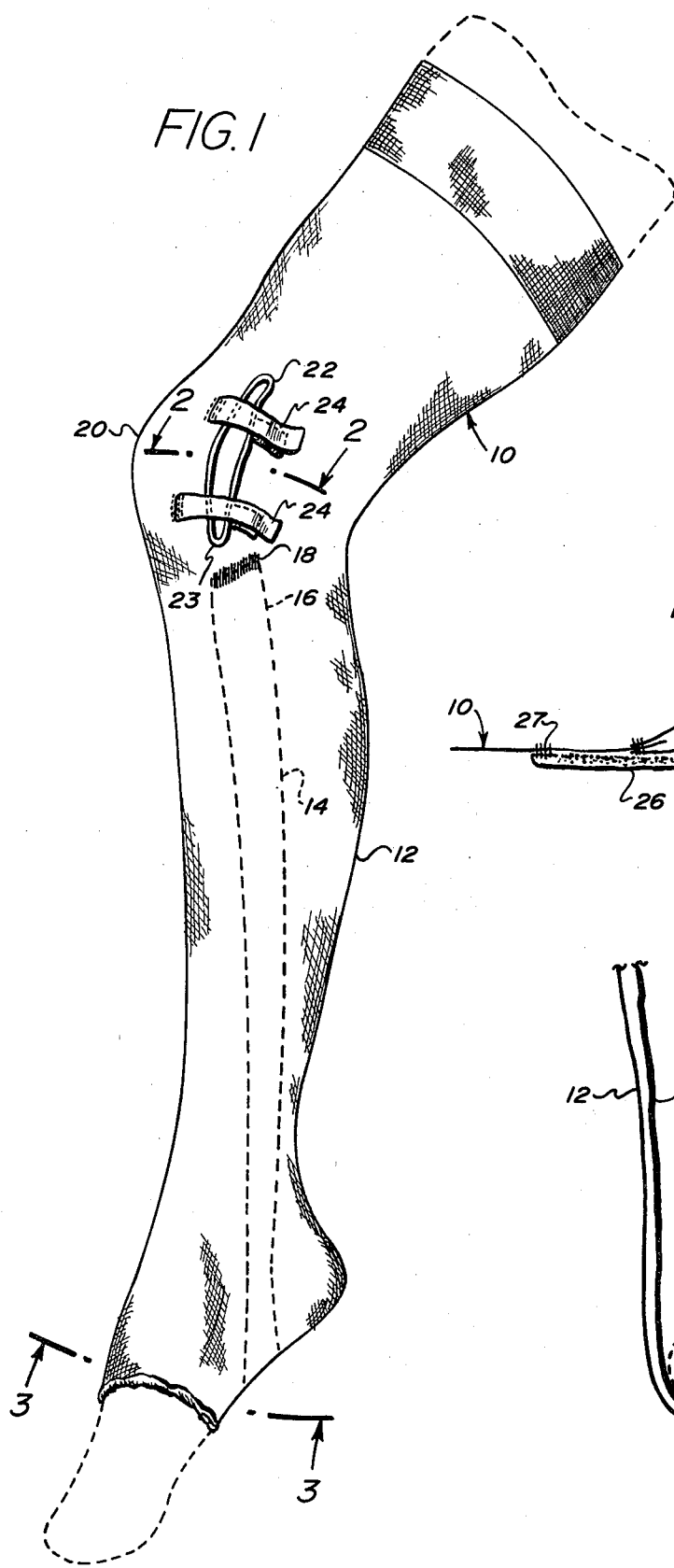
FIG. 1 is a side view of the stocking knee brace of the present invention with the knee-joint slightly flexed.
Figure 2:
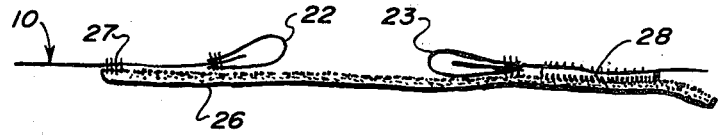
FIG. 2 is an enlarged sectional view taken along line 2—2 of FIG. 1 showing the preferred fastening mechanism for the stocking knee brace of this invention.
Figure 3:
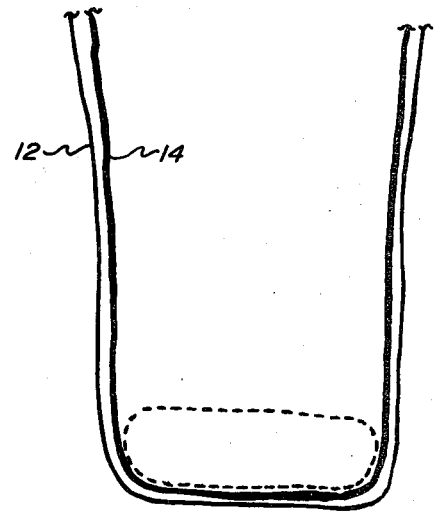
FIG. 3 is a sectional view taken along line 3—3 of FIG. 1 showing the elastic strap arrangement necessary to aid in the support of the knee-joint of the wearer of the stocking knee brace according to the present invention.

The stocking knee brace, in accordance with the present invention, includes a form fitting sheath of fabric 10 which is preferably a knitted type of material. The sheath of fabric 10 is adapted to encircle a person's leg, particularly an athlete involved in a sporting activity, from a position just below such person's ankle up to his mid-thigh region. For convenience, FIG. 1 illustrates the manner in which the stocking knee brace of this invention is worn by such person. The sheath 10 is fabric with full dimensional stretch. The sheath is sized to be smaller in length and girth of a person's leg so that the fabric is stretched as it is pulled onto the leg and into position. This helps to hold the sheath in place and imparts support, in a manner to be described hereinafter, to the person's knee-joint.

In the sheath 10, on the lower portion 12 thereof, an elastic strap 14, the ends 16 of which are anchored by stitching 17 to sheath 10 at a mid-calf region, is provided to engage the wearer's foot at his instep. The tension placed on strap 14 by such wearer's foot, which tension is transmitted to the sheath 10, cooperates with the elastic nature of the sheath fabric to help impart support to the wearer's knee-joint. Further, such cooperative support holds the knee-joint in place thus overcoming the knee's tendency to lock or separate due to a weakness which may be present in such joint.

At a mid-position along sheath 10, that portion 20 of the sheath encircling the knee-joint, vertically elongated openings 22 are provided. Such openings, one on each side of the knee-joint, are preferably about 5 to 7 cm. in length, and may be hemmed 23 to maintain the integrity of such openings. Finally, the width of said openings 22 may vary as explained hereinafter.

The purpose of said openings 22 is to permit the application of compressive pressure just above and just below the knee-joint by drawing or tightening sheath portion 20 without overlapping the sheath fabric on the wearer's leg. Such drawing or tightening is achieved by the use of fastening devices 24,24' adjacent the openings 22.

The fastening devices, two for each opening 22 located at about the top and bottom of said elongated openings 22, may comprise a fastener 26 anchored by stitching 27 to sheath portion 20, which fastener 26 is adapted to mate with a second fastener 28 anchored in similar fashion to sheath portion 20. Fasteners 26 and 28 may take the form of a burr-like material sold under the trademark "VELCRO". Fastener 26, for example, may comprise a tape having an outer face or pile of closely spaced stiff plastic spines terminating in hooks ends. The outer or hook surface adheres rapidly upon contact with many tufted textiles and also with special "VELCRO" material having a surface or pile consisting of closely spaced plastic loops. Fastener 28, for example, may comprise the latter type material. While such a simple fastening mechanism is preferred, other means of fastening are contemplated by this invention.

In utilizing the stocking knee brace of this invention, the sheath 10 is slipped over the leg such that the instep of the foot engages strap 14 and the openings 22 are on the sides of the knee-joint. While the radially stretched condition of the sheath 10, and the longitudinally stretched condition thereof resulting in part from strap 14, impart some support for the knee-joint, full support is achieved by a circumferential stretching of sheath portion 20. To effect such full support, each fastener is joined to its mating fastener with the result being to reduce the width of openings 22. Thus, said fasteners apply additional circumferential pressure to the knee-joint at positions just above and just below such knee-joint.

By this arrangement of the invention continuous support is given to the knee-joint irrespective of the flexed condition of the wearer's leg. This is particularly important for athletes who desire knee support but do not want such support at a cost or risk to maneuverability and speed.

It is anticipated that modifications may be made in the construction of the stocking knee brace of this invention and that such modifications are contemplated by the appended claims.

I claim:

1. A stocking knee brace comprising a form fitting sheath having a knee portion, shin portion, and foot portion, which sheath is adapted to encircle the leg of a person from a position below the ankle to a position above the knee, including
    (a) a U-shaped elastic strap inside said sheath, the ends of said strap being secured to said shin portion of said sheath while the strap portion intermediate said ends provides means for engaging the foot of said person,
    (b) a pair of vertically elongated openings located on opposing sides of said knee portion of said sheath, and
    (c) fastening means on said knee portion of said sheath to restrict said openings and thereby apply compressive pressure to the knee of said person.

2. The stocking knee brace according to claim 1 wherein said fastening means on said sheath comprise Velcro strips.

3. The stocking knee brace according to claim 1 wherein the longitudinal dimension of said openings, in a condition of inoperativeness, are between about 5 and 7 cm.

4. The stocking knee brace according to claim 3 wherein said fastening means on said sheath are located adjacent said openings, and wherein said fastening means are adapted to be fastened in such a manner as to apply compressive pressure just above and just below the knee-joint of said person.

5. The stocking knee brace according to claim 1 wherein said strap is in tension while engaged by the foot of said person.

* * * * *